(12) United States Patent
Anton et al.

(10) Patent No.: US 7,833,769 B2
(45) Date of Patent: Nov. 16, 2010

(54) MCRA VARIANTS AND USES THEREOF

(75) Inventors: Brian P. Anton, South Boston, MA (US); Elisabeth A. Raleigh, Somerville, MA (US)

(73) Assignee: New England Biolabs, Inc., Ipswich, MA (US)

( * ) Notice: Subject to any disclaimer, the term of this patent is extended or adjusted under 35 U.S.C. 154(b) by 681 days.

(21) Appl. No.: 11/579,227

(22) PCT Filed: Apr. 27, 2005

(86) PCT No.: PCT/US2005/014454

§ 371 (c)(1),
(2), (4) Date: Oct. 31, 2006

(87) PCT Pub. No.: WO2005/111226

PCT Pub. Date: Nov. 24, 2005

(65) Prior Publication Data

US 2008/0160513 A1 Jul. 3, 2008

Related U.S. Application Data

(60) Provisional application No. 60/568,089, filed on May 3, 2004.

(51) Int. Cl.
| | |
|---|---|
| *C07K 14/00* | (2006.01) |
| *C12Q 1/44* | (2006.01) |
| *C12Q 1/68* | (2006.01) |
| *C12N 9/16* | (2006.01) |
| *G01N 33/50* | (2006.01) |
| C07H 21/00 | (2006.01) |
| C12N 15/00 | (2006.01) |
| C12N 5/10 | (2006.01) |
| C12N 1/21 | (2006.01) |

(52) U.S. Cl. ............................ 435/196; 435/6; 435/19; 435/320.1; 435/252.3; 435/325; 530/350; 536/23.2; 436/94

(58) Field of Classification Search ............... 435/196, 435/69.1, 320.1, 19, 325, 252.3, 6; 530/350; 536/23.2

See application file for complete search history.

(56) References Cited

PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Cross et al., Nature Genetics 6(3):236-244, 1994.*
Anton et al., J. Bacteriol. 186/17: 5699-5707 (2004).
Brody et al., J. Bacteriol. 161: 1112-1117 (1985).
Bujnicki et al., Molec. Microbiol. 37: 1280-1281 (2000).
Carlson, Restriction and Modification, in Molecular Biology of Bacteriophage T4, ch. 36, p. 369, ed. Karam, ASM Press, Washington DC (1994).
Hiom et al., J. Bacteriol. 173: 7368-7373 (1991).
Laird, Nat. Rev. Cancer 3: 253-266 (2003).
Raleigh et al., Nucleic Acids Res. 16: 1563-1575 (1988).
Ramalingam et al., J. Biosci. 17: 217-232 (1992).
Shivapriya et al., Gene 157: 201-7 (1995).
Walker, The SOS Response of *Escherichia coli*, in *Escherichia coli* and Salmonella: Cellular and Molecular Biology, 2nd edition, pp. 1400-1416, ed. Neidhardt; ASM Press, Washington DC (1996).

* cited by examiner

*Primary Examiner*—Delia M Ramirez
(74) *Attorney, Agent, or Firm*—Harriet M. Strimpel (57) ABSTRACT

Compositions and methods are provided in which the composition is a protein with at least 50% but less than 100% amino acid sequence identity with McrA or is a variant McrA protein with at least one amino acid sequence modification. The variant or protein has the property of cleaving DNA with methylated cytosine and not hydroxymethylated cytosine in a target DNA sequence, or substantially lacks catalytic activity while maintaining binding activity. Methods are provided in which the protein or McrA variant are used to identify methylation sites either by cleavage or by binding to the methylation site in the presence of a marker or by binding to an immobilized protein or McrA variant.

7 Claims, 6 Drawing Sheets

FIGURE 1

| Target Sequence | nt | 123 | 456 | 789 | | | | |
| --- | --- | --- | --- | --- | --- | --- | --- | --- |
| | aa | $x_1$ | $x_2$ | $x_3$ | | | | |
| Insertion (Frame 1) | nt | 123 | 45T | GTT | TAA | ACA | 123 456 | 789 |
| | aa | $x_1$ | | | | | | |
| Insertion (Frame 2) | nt | 123 | 456 | TGT | TTA | AAC | A23 456 | 789 |
| | aa | $x_1$ | $x_2$ | | | | $x_2$ | $x_3$ |
| Insertion (Frame 3) | nt | 123 | 456 | 7TG | TTT | AAA | CA3 456 | 789 |
| | aa | $x_1$ | $x_2$ | | | | $x_2$ | $x_3$ |

DNA coding sequence of McrA (SEQ ID NO:1)

ATGCATGTTTTTGATAATAATGGAATTGAACTGAAAGCTGAGTGTTCGAT
AGGTGAAGAGGATGGTGTTTATGGTCTAATCCTTGAGTCGTGGGGGCCG
GGTGACAGAAACAAAGATTACAATATCGCTCTTGATTATATCATTGAACG
GTTGGTTGATT
CTGGTGTATCCCAAGTCGTAGTATATCTGGCGTCATCATCAGTCAGAAAA
CATATGCATTCTTTGGATGAAAGAAAAATCCATCCTGGTGAATATTTTACT
TTGATTGGTAATAGCCCCCGCGATATACGCTTGAAGATGTGTGGTTATCA
GGCTTATTT
TAGTCGTACGGGGAGAAAGGAAATTCCTTCCGGCAATAGAACGAAACGA
ATATTGATAAATGTTCCAGGTATTTATAGTGACAGTTTTTGGGCGTCTATA
ATACGTGGAGAACTATCAGAGCTTTCACAGCCTACAGATGATGAATCGCT
TCTGAATATGAGGGTTAGTAAATTAATTAAGAAAACGTTGAGTCAACCCG
AGGGCTCCAGGAAACCAGTTGAGGTAGAAAGACTACAAAAAGTTTATGT
CCGAGACCCGATGGTAAAAGCTTGGATTTTACAGCAAAGTAAAGGTATA
TGTGAAAACTGTGGTAAAAATGCTCCGTTTTATTTAAATGATGGAAACCC
ATATTTGGAAGTACATCATGTAATTCCCCTGTCTTCAGGTGGTGCTGATA
CAACAGATAACTGTGTTGCCCTTTGTCCGAATTGCCATAGAGAATTGCAC
TATAGTAAAAATGCAAAAGAACTAATCGAGATGCTTTACGTTAATATAAA
CCGATTACAGAAATAA

FIGURE 5B

Translated protein sequence (SEQ ID NO:2)

MHVFDNNGIE LKAECSIGEE DGVYGLILES WGPGDRNKDY
    NIALDYIIER
LVDSGVSQVV VYLASSSVRK HMHSLDERKI HPGEYFTLIG
    NSPRDIRLKM
CGYQAYFSRT GRKEIPSGNR TKRILINVPG IYSDSFWASI IRGELSELSQ
PTDDESLLNM RVSKLIKKTL SQPEGSRKPV EVERLQKVYV
    RDPMVKAWIL
QQSKGICENC GKNAPFYLND GNPYLEVHHV IPLSSGGADT
    TDNCVALCPN
CHRELHYSKN AKELIEMLYV NINRLQK

US 7,833,769 B2

SEQUENCE LISTING

<160> NUMBER OF SEQ ID NOS: 2

<210> SEQ ID NO 1
<211> LENGTH: 834
<212> TYPE: DNA
<213> ORGANISM: Escherichia coli
<220> FEATURE:
<221> NAME/KEY: misc_feature
<223> OTHER INFORMATION: Strain K12

<400> SEQUENCE: 1
atgcatgttt ttgataataa tggaattgaa ctgaaagctg agtgttcgat aggtgaagag    60
gatggtgttt atggtctaat ccttgagtcg tgggggccgg gtgacagaaa caaagattac   120

-continued

```
aatatcgctc ttgattatat cattgaacgg ttggttgatt ctggtgtatc ccaagtcgta    180
gtatatctgg cgtcatcatc agtcagaaaa catatgcatt ctttggatga agaaaaaatc    240
catcctggtg aatattttac tttgattggt aatagccccc gcgatatacg cttgaagatg    300
tgtggttatc aggcttattt tagtcgtacg gggagaaagg aaattccttc cggcaataga    360
acgaaacgaa tattgataaa tgttccaggt atttatagtg acagtttttg ggcgtctata    420
atacgtggag aactatcaga gctttcacag cctacagatg atgaatcgct tctgaatatg    480
agggttagta aattaattaa gaaaacgttg agtcaacccg agggctccag gaaaccagtt    540
gaggtagaaa gactacaaaa agtttatgtc cgagacccga tggtaaaagc ttggatttta    600
cagcaaagta aagtatatg tgaaaactgt ggtaaaaatg ctccgttttta tttaaatgat    660 ggaaacccat atttggaagt acatcatgta attcccctgt cttcaggtgg tgctgataca    720
acagataact gtgttgccct ttgtccgaat tgccatagag aattgcacta tagtaaaaat    780
gcaaaagaac taatcgagat gctttacgtt aatataaacc gattacagaa ataa          834
```

<210> SEQ ID NO 2
<211> LENGTH: 277
<212> TYPE: PRT
<213> ORGANISM: Escherichia coli
<220> FEATURE:
<221> NAME/KEY: MISC_FEATURE
<223> OTHER INFORMATION: Strain K12

<400> SEQUENCE: 2

```
Met His Val Phe Asp Asn Asn Gly Ile Glu Leu Lys Ala Glu Cys Ser
1               5                   10                  15

Ile Gly Glu Glu Asp Gly Val Tyr Gly Leu Ile Leu Glu Ser Trp Gly
            20                  25                  30

Pro Gly Asp Arg Asn Lys Asp Tyr Asn Ile Ala Leu Asp Tyr Ile Ile
        35                  40                  45

Glu Arg Leu Val Asp Ser Gly Val Ser Gln Val Val Tyr Leu Ala
    50                  55                  60

Ser Ser Ser Val Arg Lys His Met His Ser Leu Asp Glu Arg Lys Ile
65                  70                  75                  80

His Pro Gly Glu Tyr Phe Thr Leu Ile Gly Asn Ser Pro Arg Asp Ile
                85                  90                  95

Arg Leu Lys Met Cys Gly Tyr Gln Ala Tyr Phe Ser Arg Thr Gly Arg
            100                 105                 110

Lys Glu Ile Pro Ser Gly Asn Arg Thr Lys Arg Ile Leu Ile Asn Val
        115                 120                 125

Pro Gly Ile Tyr Ser Asp Ser Phe Trp Ala Ser Ile Ile Arg Gly Glu
    130                 135                 140

Leu Ser Glu Leu Ser Gln Pro Thr Asp Asp Glu Ser Leu Leu Asn Met
145                 150                 155                 160

Arg Val Ser Lys Leu Ile Lys Lys Thr Leu Ser Gln Pro Glu Gly Ser
                165                 170                 175

Arg Lys Pro Val Glu Val Glu Arg Leu Gln Lys Val Tyr Val Arg Asp
            180                 185                 190

Pro Met Val Lys Ala Trp Ile Leu Gln Gln Ser Lys Gly Ile Cys Glu
        195                 200                 205

Asn Cys Gly Lys Asn Ala Pro Phe Tyr Leu Asn Asp Gly Asn Pro Tyr
    210                 215                 220

Leu Glu Val His His Val Ile Pro Leu Ser Ser Gly Gly Ala Asp Thr
```

-continued

```
225                 230                 235                 240
Thr Asp Asn Cys Val Ala Leu Cys Pro Asn Cys His Arg Glu Leu His
                245                 250                 255

Tyr Ser Lys Asn Ala Lys Glu Leu Ile Glu Met Leu Tyr Val Asn Ile
            260                 265                 270

Asn Arg Leu Gln Lys
        275
```

MCRA VARIANTS AND USES THEREOF

CROSS REFERENCE

This application is a §371 application of international application No. PCT/US2005/014454 filed on Apr. 27, 2005, which claims priority from U.S. provisional application No. 60/568,089 filed on May 3, 2004, herein incorporated by reference.

BACKGROUND

The locations and patterns of methylated residues in DNA play an important role in many areas of biological research, not least in epigenetics and oncology. Epigenetic patterns of modification control the structure of chromatin, and thereby regulate gene expression. Methylation of DNA at specific sites can prevent the binding of transcription factors (a direct effect), or groups of methylated sites can attract methyl-binding domain (MBD) proteins, which act in concert with histone deacetylases to alter chromatin structure and silence gene expression (an indirect effect). Regions in mammalian genomes rich in CG dinucleotides, called CpG islands, are often indicative of methylation resistance and active gene expression. Abnormal methylation patterns have been associated with cancer due to resultant changes in gene expression. Large-scale investment in the "Human Epigenome Project" (HEP), an effort to map sites of cytosine methylation in the human genome, attests to the growing importance of knowledge of patterns and sites of DNA methylation.

Several technologies for analyzing methylated DNA are available at present. These include analyzing overall methylation content of a DNA sample (e.g., a genome), the degree of methylation at a particular site in a sample, and the pattern of methylation of multiple sites in cis on a DNA strand in a particular region, or on profiles of methylation at selected sites throughout the genome. The technologies to achieve the above largely depend on restriction digestion or bisulfite conversion (Laird, P. W. Nat Rev Cancer 3, 253-266 (2003)).

Conventional restriction digestion relies on the fact that methylation at or near restriction endonuclease sites can block cleavage by those nucleases. Differing methylation patterns, therefore, will cause differences in the patterns of cleavage by various restriction enzymes. One of the oldest techniques for examining the products of these restriction digests is the Southern blot. This process is relatively time-consuming, however, and requires a large amount of DNA for analysis. Furthermore, determination of precise methylation sites is dependent on a priori knowledge of the sequence being examined unless an appropriate unmethylated control sample is available. In addition, "Lack of cleavage" is a less desirable method of detection than provided by modified cytosine restriction A (McrA) because inactive enzyme or incomplete digestion can lead to a false positive result.

Treatment of DNA with sodium bisulfite converts unmethylated, but not methylated, cytosine to uracil over short timespans. Many techniques have been developed to exploit this phenomenon, but by far the most common bisulfite-based methods involve amplification of converted DNA by PCR and sequencing. While this method allows for the precise identification of methylation sites, it precludes the analysis of a large number of noncontiguous methylation sites simultaneously. Identifiable sites in a given experimental reaction must be within a single PCR amplicon, or at best a moderate number of amplicons afforded by multiplex PCR.

SUMMARY

In an embodiment of the invention, a variant of an McrA protein is described having a binding domain, and optionally a catalytic domain; the McrA having an amino acid sequence substantially identical to SEQ ID NO:2, the variant of the McrA having a modification in the amino acid sequence so as to provide (a) an altered catalytic activity being capable of cleaving DNA with methylated cytosine and not hydroxymethylated cytosine in a target sequence or (b) substantially no catalytic activity while maintaining binding activity.

The modification in the amino acid sequence may result from a mutated gene encoding the McrA protein variant wherein the mutated gene contains one or more mutations in a region of the McrA DNA having a sequence corresponding to SEQ ID NO:1.

The modification contained in the McrA variant may result from a mutated gene encoding the McrA protein wherein the mutated gene contains one or more mutations in a region of the DNA corresponding to amino acids 149-177 in SEQ ID NO:1. Alternatively, the modification may be a chemical modification of the McrA protein, in which the catalytic activity is inhibited while the binding activity remains intact.

In an embodiment of the invention, a method is provided for identifying variants of Mcr endonucleases defective in cleavage activity but retaining DNA binding activity. The method includes the steps of: (a) introducing into the DNA sequence of a protein alignable with the McrA protein of SEQ ID NO:1, a mutation selected from a C-terminal truncation ending at or after amino acid 149 or a deletion, insertion or modification of one or more amino acids in a region corresponding to amino acids 149-277 of the McrA protein; and (b) assaying the phenotype by: (i) preventing or allowing growth of Lambda phage with DNA methylated with one or more sequence-specific methyltransferase; or (ii) determining induction of a LexA regulon; and (c) identifying those active in (i) but inactive or with reduced activity in (ii).

In an embodiment of the invention, a method is provided for separating methylated DNA from unmethylated DNA. The method has the following steps: (a) immobilizing one or more McrA variants described above; (b) contacting the immobilized mutant McrA with a DNA sample; (c) selectively binding DNA containing methylated cytosine residues; and (d) separating methylated DNA from unmethylated DNA.

In an embodiment of the invention, a method is provided for identifying methylated DNA that includes the steps of: (a) binding one or more McrA variants described above to a methylated DNA substrate; (b) identifying the extent and optionally the location of binding of the one or more McrA variants by means of a reporter; and (c) identifying the methylated DNA. Examples of the reporter include a fluorescent, chemiluminescent or radioactive tag.

An embodiment of the invention is a method for selectively cleaving methylated DNA by mixing DNA with a preparation of McrA under conditions suitable for cleavage of the DNA at methylated nucleotide sequences in the DNA. Examples of the methylated sequences include $C^{5m}CGG$, $C^{5m}CSGG$ and $^{5M}CG$.

In an embodiment of the invention, a protein or DNA encoding he protein is provided where the protein has a binding domain and optionally a catalytic domain: wherein the protein has an amino acid sequence of at least 50% identity with respect to SEQ ID NO:2: the protein having (i) catalytic activity capable of cleaving DNA with methylated cytosine and not hydroxy methylated cytosine in a target DNA sequence; or (ii) substantially lacking catalytic activity while maintaining binding activity.

BRIEF DESCRIPTION OF THE FIGURES

FIG. 1 shows nucleotides and amino acids added following transposon insertion and subsequent removal with PmeI. Three codons of target sequence are shown, with numerals representing specific bases. x1, x2 and x3 represent the amino acids encoded by codons "123", "456", and "789", respectively. Insertion occurs in one of three reading frames: frame 1 (following base 5), frame 2 (following base 6), or frame 3 (following base 7). The 5 base target site duplication that results from the transposon insertion is underlined, and the amino acids added relative to the original sequence are boxed in gray. Some added amino acids are invariant, whereas others (represented by a, b, g, d) are variable and dependent on the target sequence. Insertions in frame 1 almost always result in premature truncation of the expressed protein. However, in the rare case where codon "456" is itself a stop codon, an insertion in frame 1 will actually add two residues (eV, where e=Y, C) to the C-terminus of the expressed protein rather than truncate prematurely. Key: a=any amino acid except M, E, K, Q, or W (in approximately 75% of cases it will be x2); b=I, K, M, N, R, S, or T; g=L, M, or V; d=H or Q.

FIG. 2 shows a schematic location of GPS-LS insertions in the mcrA gene. The large horizontal arrow represents mcrA; some of the immediate upstream region is also shown. Vertical arrows above the gene represent amino acid insertion variants (frames 2 and 3), and arrows below the gene represent truncation variants (frame 1). Black arrows are RglA– or McrA–, dashed arrows RglAi or McrAi, and gray arrows RglA+ or McrA+. The region responsible for DNA binding and catalysis are indicated. The insertion of mutant 1-75 is marked with an asterisk (*).

Lanes 1 and 10 are molecular weight standards.
Lane 2 shows an un-induced E. coli crude extract in which no fusion protein is visible.
Lanes 3, 4, and 5 show crude extract after induction with 0.3 mM
isopropyl-β-D-thiogalactopyranoside (IPTG) for 3 hours at 37° C., 4 hours at 30° C., and 24 hours at 16° C., respectively.
Lanes 6, 7, and 8 show the soluble fraction of lanes 3, 4, and 5, respectively.

DETAILED DESCRIPTION

Some naturally occurring enzymes are capable of cleaving DNA specifically at or near methylated nucleotide sequences. These include the Type II restriction enzyme DpnI and Mcr endonucleases McrBC and McrA (Type IV restriction endonucleases). McrBC has been relatively well characterized, but its specificity determinants are weak. It recognizes two half-sites of the form $R^mC$, which can be separated by 55 bases to 3000 bases.

In contrast to McrBC, McrA binds and cleaves at a single site, which may be methylated or hydroxymethylated. For example, McrA cleaves at sites methylated by M.HpaII ($C^{5m}CGG$), M.SssI ($^{5m}CG$), or M.Eco1831I ($C^{5m}CSGG$). The mcrA gene has been cloned and found to encode a 31 kDa protein product with 277 residues (Hiom, K., and S. G. Sedgwick *J. Bacteriol.* 173:7368-7373 (1991); Ramalingam, R., et al. *J. Biosci.* 17:217-232 (1992)). It is normally expressed at low levels in the cell, and regulation at the translational level has been suggested (Shivapriya, R. et al. *Gene* 157:201-7 (1995)). McrA has no close homologues in public sequence databases (Brody, H., et al., *J. Bacteriol.* 161:1112-1117 (1985)), but two conserved motifs have been noted in its carboxy-terminal domain.

Figure 2:
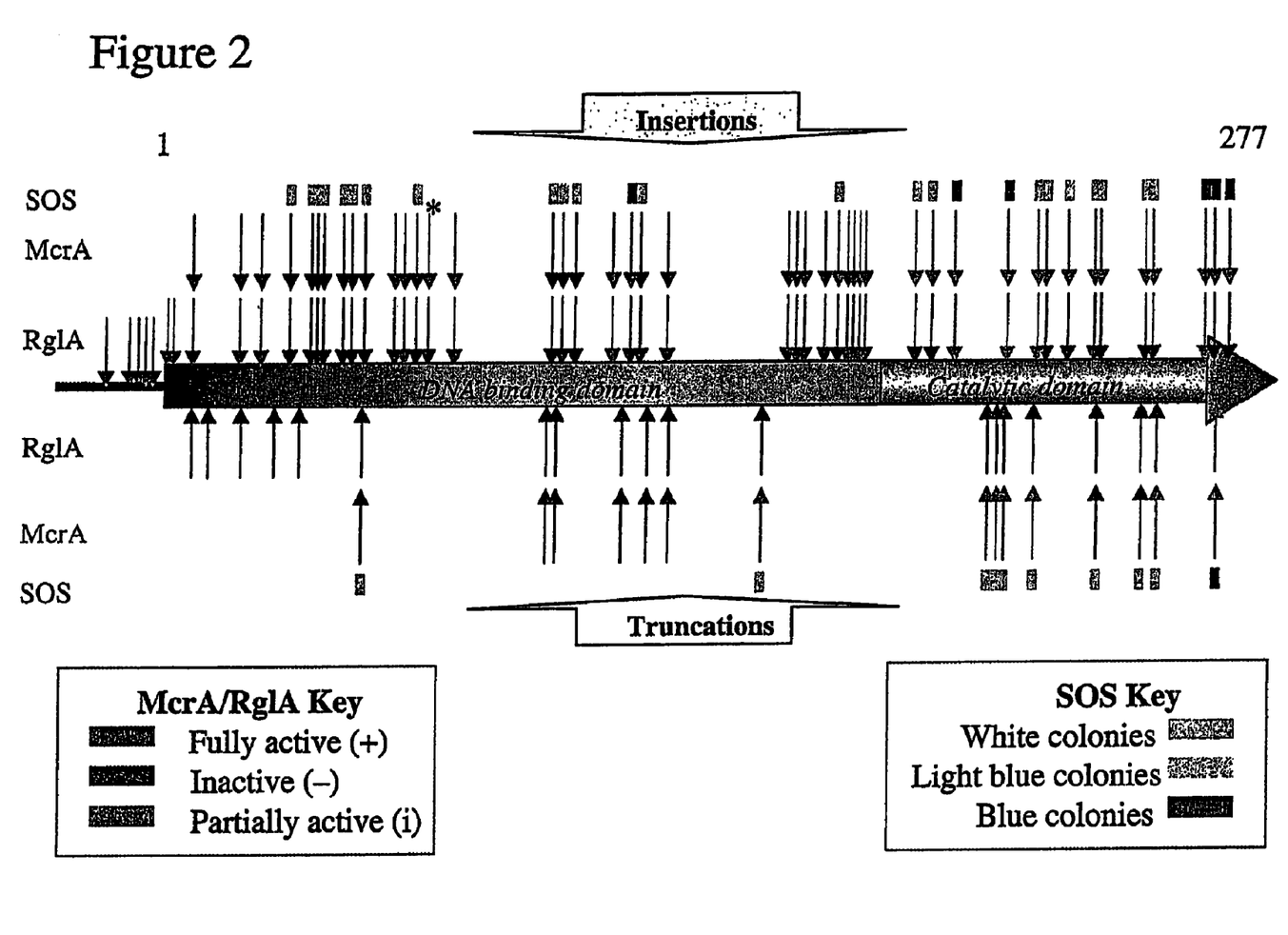
Figure 3:
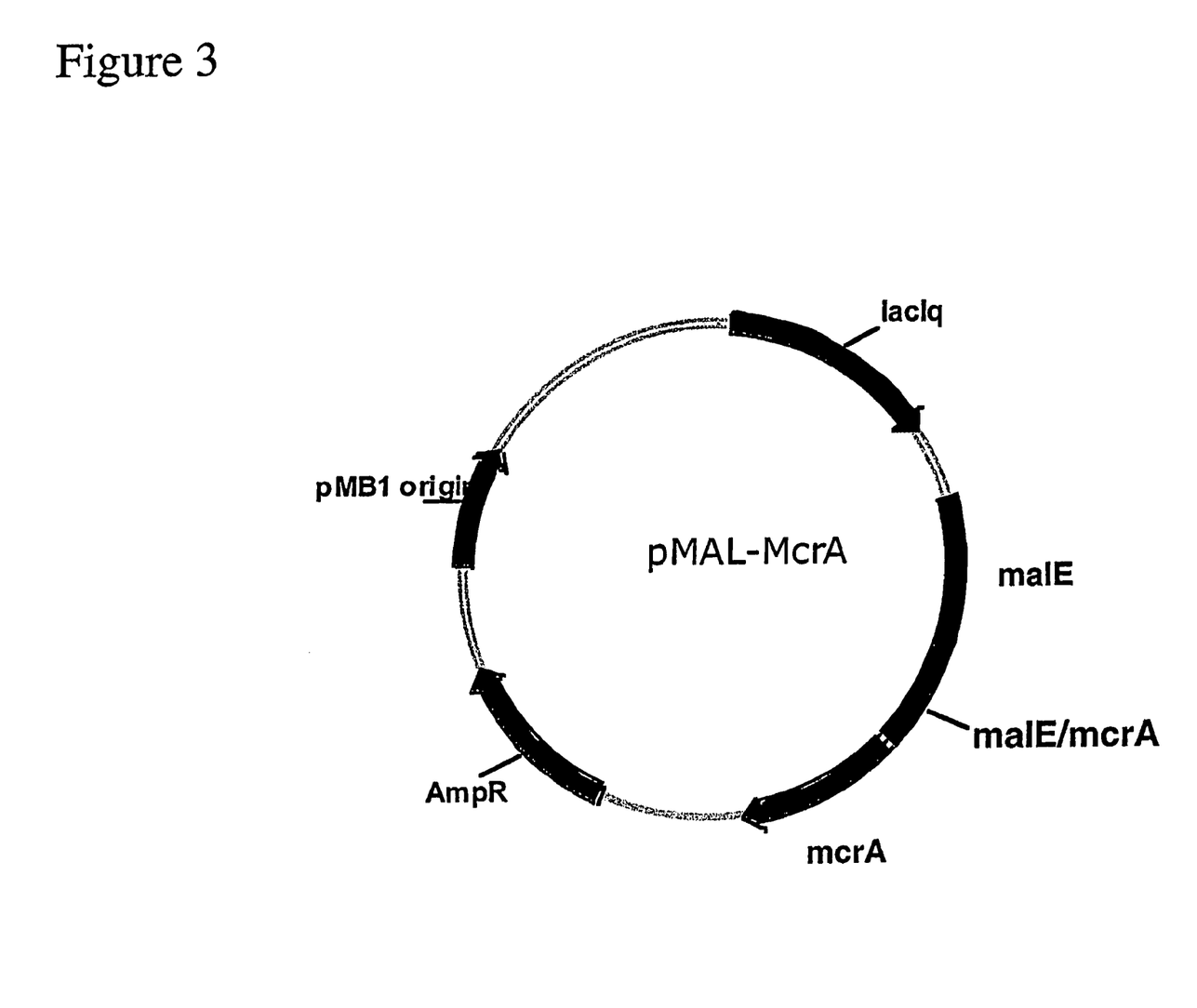
FIG. 3 shows a cartoon of pMAL-McrA.
Figure 4:
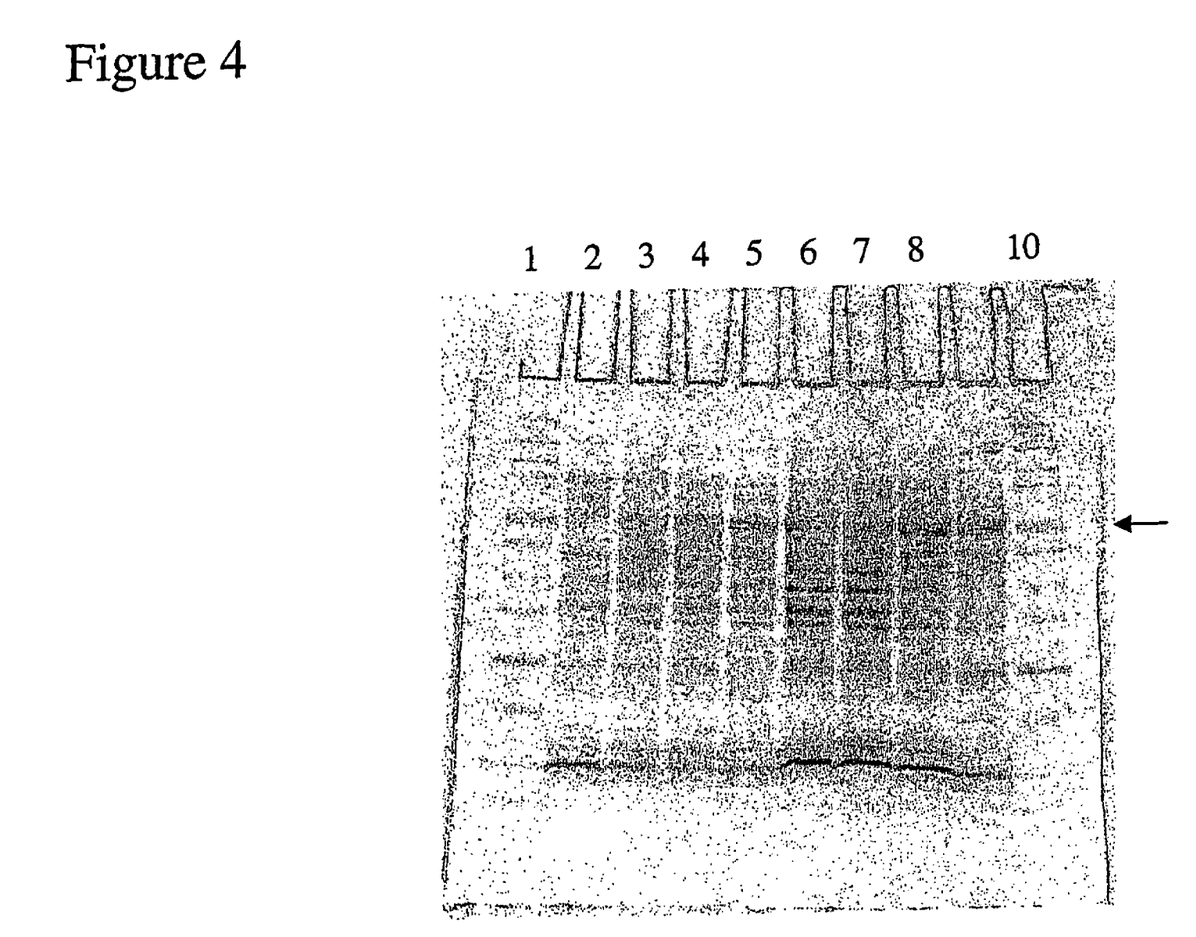
FIG. 4 shows the expression of the maltose-binding protein-McrA (MBP-McrA) fusion protein (size indicated by the arrow) from pMAL-McrA on a Coomassie-stained protein gel.
Figure 5A:
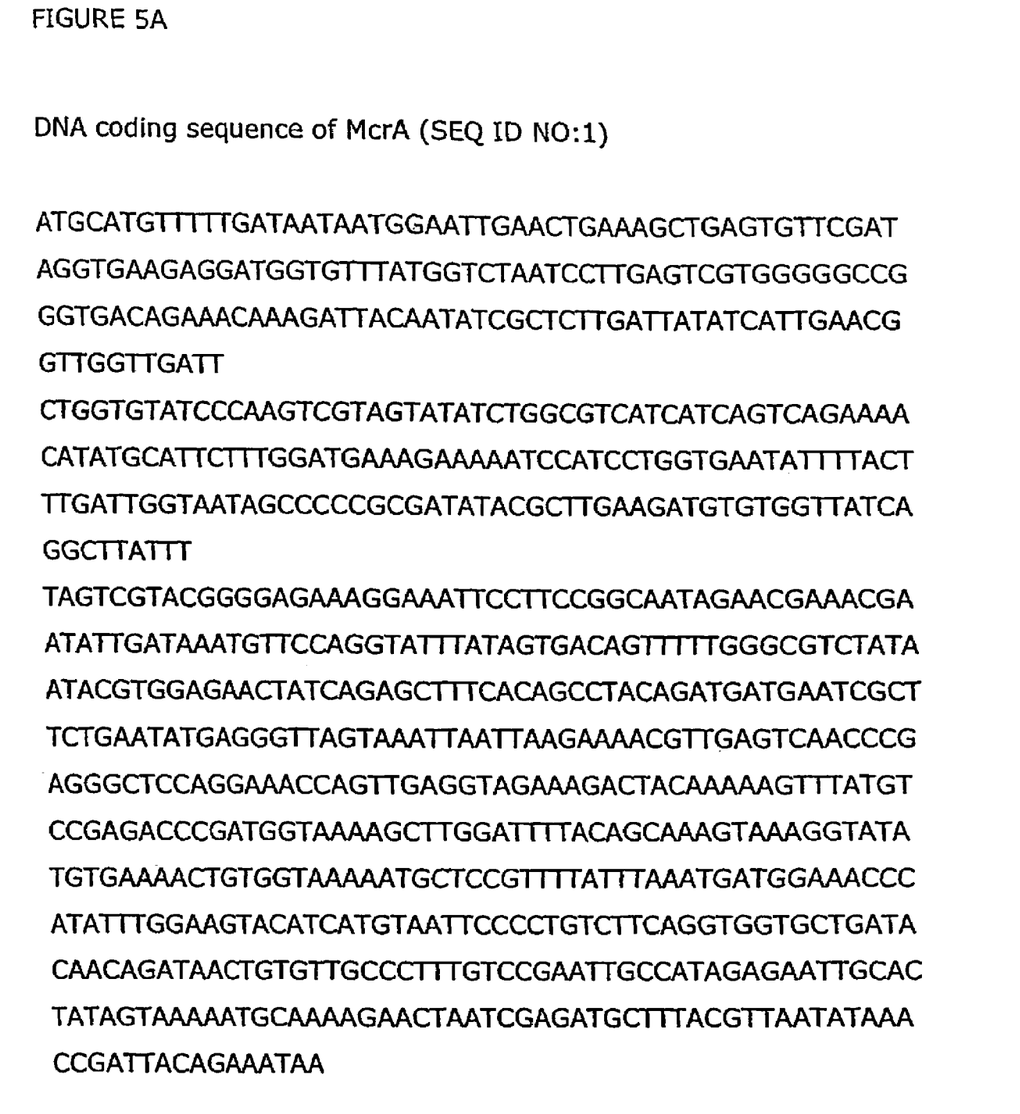
FIG. 5A is a DNA sequence encoding McrA (SEQ ID NO:1).
Figure 5B:
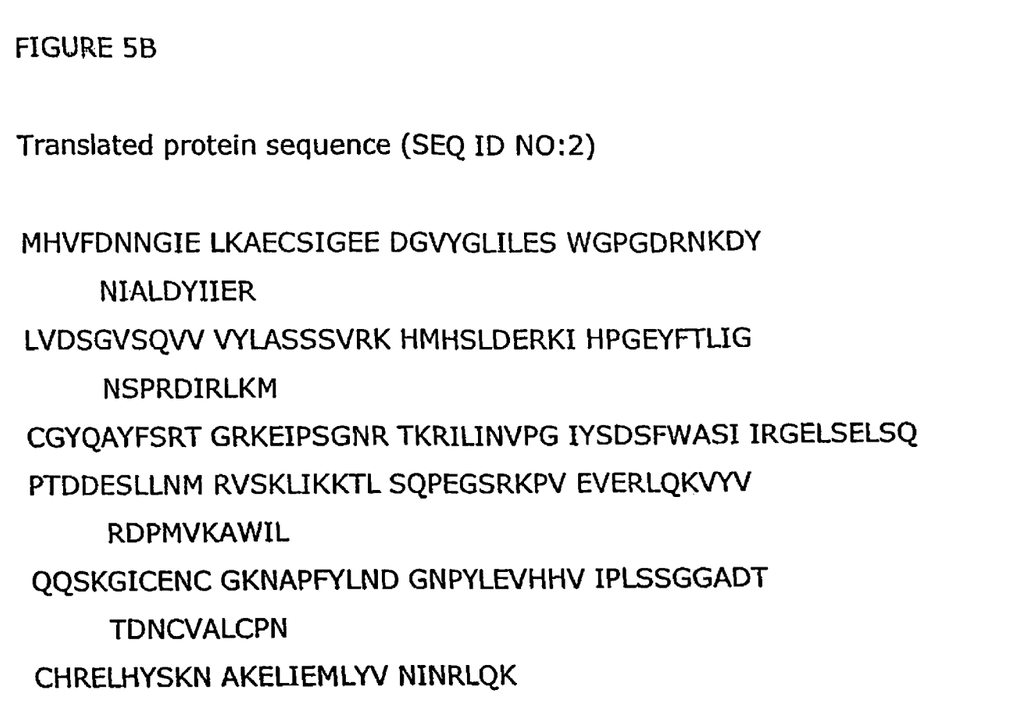
FIG. 5B is an amino acid sequence for McrA (SEQ ID NO:2).

McrA enzyme is here shown to be modular with the DNA binding and specificity determinants in the N-terminal domain and the catalytic apparatus in the C-terminal domain as shown in FIG. 2. The N-terminal domain alone appears capable of binding specifically to methylated DNA sequences.

One embodiment of the invention is the use of one or more McrA or McrA variants for binding and cleaving specific methylated sites on DNA for the purposes of epigenetic mapping. McrA proteins and variants that retain cleavage activity have the ability to cleave DNA in response to methylated sites. In addition, these McrA proteins and variants are capable of recognizing and cleaving a variety of different sequences containing methylated cytosine as illustrated by the sites specified above.

Variants of McrA result from mutations in the DNA encoding the protein or by chemical modification of the protein. A mutation in a DNA sequence can include one or more of a deletion, an insertion or a replacement. A chemical modification includes binding of a chemical moiety to the protein to alter protein structure and/or charge, thereby disrupting cleavage, but not binding. Methods known in the art to generate mutations in DNA may be used. In the Examples, insertion-scanning mutagenesis is used to generate mutations in Table 2.

An additional approach to epigenetic mapping uses McrA variants that retain their binding properties and have a modified, but active cleavage function or no cleavage function. Fusion of these McrA variants to a reporter allows for the identification of methylated DNA in situ without cleavage. In an embodiment of the invention, McrA is labeled by standard techniques using, for example, fluorescent, radioactive, chemiluminescent or colored markers such that the methylated sites on DNA can be visualized in situ. Detection of signal from the reporter function would indicate the presence of methylation at an McrA-sensitive site somewhere on the associated DNA fragment, and prior knowledge of expected fragment sizes would not be required for this determination.

Immobilizing an McrA variant by means of fusion to a second binding domain capable of binding an affinity substrate provides a reagent for separating out methylated DNA. For example, the second binding domain may be any of a MBP, a chitin-binding domain (CBD), a His tag or other binding molecule for immobilization on a substrate. McrA binding domain may be immobilized on any of a column, a plate, a membrane, a bead or a porous substrate where the substrate is made from a suitable material. For example, if MBP is utilized, the substrate may be made from amylose or if a CBD is utilized, then the substrate may be chitin.

The binding of McrA variants to a specific DNA sequence containing the methylated CpG dinucleotide provides a means for separating DNA fragments with varying amounts of methylation. The cells from which the substrate DNA may be obtained include prokaryotic, eukaryotic or archeal cells. Examples of eukaryotic cells include plant cells as well as animal cells.

In an embodiment of the invention, McrA variants that lack an active cleavage domain have been obtained after characterizing the functional domain architecture of McrA genetically using insertion-scanning mutagenesis. A systematic analysis of the functional organization of McrA, using GPS-LS insertion scanning mutagenesis produced insertion mutants which contained additional contiguous amino acids interpolated at random locations within the polypeptide chain. The effect of these insertions on the structure of the protein and its activity was analyzed and found to vary according to the location and composition of the inserted residues.

The Examples show the results obtained when in-frame insertions of five amino acids were introduced into 46 independent locations and C-terminal truncations were made at 20 independent locations in the McrA protein. Each mutant was assayed for in vivo restriction of both methylated and hydroxymethylated bacteriophage (M.HpaII-modified λ and T4gt, respectively) and for induction of the *E. coli* SOS response in the presence of M.HpaII methylation, indicative of DNA damage (Walker, G. C., "The SOS Response of *Escherichia coli*," in *Escherichia coli and Salmonella*: Cellular and Molecular Biology, 2nd edition, pp. 1400-1416, ed. Neidhardt, F. C.; ASM Press, Washington, D.C., 1996). The results showed that McrA has an N-terminal DNA-binding domain and a C-terminal catalytic nuclease domain connected by a linker region largely tolerant of amino acid insertions. In addition, DNA damage inflicted by a functional C-terminal domain in the presence of a functional N-terminal domain gave rise to restriction of phage T4gt and M.HpaII-modified λ. Disruption of the N-terminal domain abolished restriction of both substrates. Surprisingly, truncation mutants that spared the N-terminal domain did not mediate DNA damage as measured by SOS induction but nevertheless partially restrict M.HpaII-modified λ in vivo.

A single variant was additionally obtained which had an insertion in the N-terminal domain and which could fully restrict λ but did not restrict T4gt. This variant appears to be selectively impaired in its substrate recognition so that it is capable of distinguishing methylated from hydroxymethylated substrates.

The C-terminal domain of McrA contains three histidine residues (H-228, H-252 and H-256) predicted to coordinate the $Mg^{2+}$ ion as well as four cysteine residues (C-207, C-210, C-248 and C-251) which form a putative zinc finger most likely involved in stabilizing the structure. All C-terminal truncations within this region abolished RglA activity and SOS induction with the exception of isolate 3-7 (Table 3), which lacks only the extreme C-terminal 9 residues. This last mutant shows an intermediate phenotype ($RglA^i$ $McrA^i$). Within the modeled region of McrA, only amino acid insertions after residues 159, 167, 174, and 177 resulted in full activity ($RglA^+McrA^+$). Six other amino acid insertion mutants retained partial restriction activity (after residues 203, 217, 224, 266, 267, and 271) and also induced the SOS response. The remaining 9 insertions in this region, many of which are located within putative helices or proximal to metal ion-coordinating residues, abolished both RglA restriction and SOS induction completely.

Between residues 28 and 124 of McrA, a majority of insertions (12 of 18) were inactive in all tests consistent with catalytic activity residing at the C-terminal end of McrA. Also consistent with this model, the extreme N-terminus (residues 1-20) and the putative interdomain connector region (residues 128 to 177) were highly tolerant of the 5-residue insertions generated in this study. Variants with insertions in the extreme C-terminus, on the other hand, suffered partial loss of both restriction activities. Distortion of this region by insertion may be the cause of loss of or reduced affinity for magnesium ion.

Indeed, it is here proposed that backbone distortion of McrA dominates over side-chain effects as determined from the effect of inserting 5 amino acid residues at different locations within the protein. In 4 variants, different sets of amino acids were introduced at the same location after residues 38, 174, 177, and 235. In all 4 cases, the phenotypes of both insertions were identical.

Separation of Restriction Phenotypes

All variants that exhibited phenotype separation were $RglA^-$ of which one retained full $McrA^+$ activity. The remaining 16 showed partial activity ($McrA^i$) and were all located in the C-terminal half of the protein. Six of these were truncation mutants, most comparable to the HindIII fill-in mutants reported earlier. 15 of these 16 $McrA^i$ mutants (including all of the truncations) were also white in the SOS-reporting strain, and therefore not able to inflict DNA damage in the presence of HpaII-methylated DNA, the presumed target of restriction.

For these 15 mutants, the separation of phenotype reflects loss of cleavage activity but not DNA binding activity for both targets. The residual "restriction" phenotype is due to interference with phage development by binding rather than cleavage. The RglA and McrA phenotype assays differ in two fundamental ways: the type of bacteriophage (T4 or λ) used for the assay and the type of DNA modification present (5-hydroxymethylcytosine or 5-methylcytosine). A DNA binding protein acting at a critical site on an infecting λ genome can disrupt phage development efficiently, while the same protein bound to an infecting T4 genome might be without effect.

The boundaries of the DNA binding domain are delineated by truncation mutants 4-13 (residue 129, null phenotype) and 2-24 (residue 149, $RglA^-McrA^i$/white; Table 3): the first 130-149 residues are required to confer $McrA^i$, and for functional DNA binding activity.

Partial-Restriction Phenotypes

Variants that only partially disrupt the catalytic domain should be capable of partially restricting both T4gt and I.HpaII as well as inducing SOS. This combination of properties was observed in the four $RglA^iMcrA^i$ variants, all with insertions in the proposed catalytic domain.

One $RglA^-McrA^i$ insertion-variant near the border of the proposed binding domain (residue 122) retained blue color in the SOS reporter strain. This variant retained limited cleavage activity.

Three insertion variants were found to be $RglA^-McrA^-$, but gave a pale blue color on X-gal. These variants lie within the proposed boundaries of the DNA binding domain. Another variant 1-75 is $RglA^-$ and $McrA^+$. Moreover, this variant cannot be stably maintained in the presence of M.HpaII expression: both blue and white colonies are observed on X-gal in the SOS induction assay, presumably resulting from strong selection for further mutations that inactivate the enzyme completely. This mutation is a 5-residue insertion in the proposed DNA binding domain. This mutation may disable the recognition of hydroxymethylated but not methylated substrates.

The separation of the N-terminal DNA binding domain and a C-terminal cleavage domain in McrA is consistent with the ease with which many variants can be generated, coupled with a variety of phenotypic assays.

All references cited herein are incorporated by reference. Additionally, provisional application U.S. Ser. No. 60/568, 089. filed May 3, 2004, Carlson, "Restriction and Modification" in Molecular Biology of Bacteriophage T4, ch 36, p. 369, ed. Karam, J. D.; ASM Press, Washington, D.C., 1994 and Anton et al. *J. Bacteriol* 186/17:5699-5707 (2004) are herein incorporated by reference.

EXAMPLES

Example 1

Formation of Mutants by Linker Scanning Mutagenesis

Bacterial Strains and Media. pJEK8 plasmid construction was carried out in *E. coli* strains ER2683 (fhuA2 glnV44 e14-rfbD1? relA1? endA1 spoT1? thi-1 Δ(mcrC-mrr)114:: IS10 Δ(lacI-lacA)200 F' proAB lacI$^q$ ΔlacZM15 (Kan$^R$) miniTn10) and ER1793 (fhuA2 Δ(lacZ)r1 glnV44 e14-trp-31 his-1 rpsL104 xyl-7 mtl-2 metB1 Δ(mcrC-mrr)114::IS10; (Sibley, M. and Raleigh, E. A., *Nucleic Acids Res*. 32:522-534 (2004)), grown in Luria (Brooks, J. E., et al. *Nucleic Acids Res*. 17:979-997 (1989)) or Luria-Bertani (Silhavy, T. J., et al. *Experiments with gene fusions*, Cold Spring Harbor Laboratory, Cold Spring Harbor, N.Y., p. 217(1984)) medium supplemented with ampicillin. Cultures for other plasmid preparations were carried out in ER1793 grown in Luria-Bertani medium supplemented with antibiotics as necessary. Phage restriction assays were also performed in ER1793 grown in lambda broth (Kleckner, N., et al. *Genetics* 90:427-61 (1978)) supplemented with 20 µg/ml ampicillin. Bacteriophage were diluted in a 9:1 mixture of Idil (10 mM Tris-HCl, pH 7.5, 10 mM MgSO$_4$) and 100 mM MgSO$_4$.

DNA damage assays were carried out in *E. coli* strain ER2171 (fhuA2 D(argF-lac)U169 glnV44 e14-trp-31 his-1 rpsL104 xyl-7 mtl-2 metB1 dinD2::MudI1734 (Kan$^R$, LacZ (ts)) D(mcrC-mrr)114::IS10) containing pACYC-MHpaII grown on Luria medium supplemented with ampicillin, chloramphenicol, and 40 µg/ml 5-bromo-4-chloro-3-indolyl b-D galactopyranoside (X-gal). ER2171 was constructed by introducing the dinD::lacZ reporter of AP1-200 (Piekarowicz, A., et al. *J. Bacteriol*. 173:150-155 (1991)) into ER1996 (Mi, S., and R. J. Roberts. *Nucleic Acids Res* 20:4811-6 (1992)). The reporter allele in AP1-200 was found to be temperature-sensitive for b-galactosidase activity, unlike the parental reporter (Heitman, J., and P. Model. *J. Bacteriol*. 169:3243-3250 (1987)). A nalidixic acid gradient causes dose-dependent induction of blue color on X-gal at 30° or 37° C., but at 42° strains carrying this allele are white regardless of DNA damage. The β-galactosidase activity is low enough that uninduced colonies are white at low temperature, where the parental reporter gives a light blue color in the uninduced state that grows darker with age. This background reduction improves discrimination between colonies suffering DNA damage and those not when tested at 37° or below. This allele carries a mutation resulting in lower specific activity of the β-galactosidase moiety even at permissive temperatures.

Enzymes and general techniques. All enzymes were from New England Biolabs, Inc., Beverly, Mass., and used according to the manufacturer's instructions. Plasmids were isolated using the QIAprep Spin Miniprep Kit (Qiagen, Inc., Valencia, Calif.) or the Compass Mini Plasmid Prep Kit (American Bioanalytical, Inc., Natick, Mass.). Plasmid pNEB193 was from New England Biolabs, Inc., Beverly, Mass.

Plasmid construction. pJEK8 was constructed from pER137, which has been described previously (Raleigh, E. A., et al. *Genetics* 122:279-296 (1989)), in several steps. The resulting construct (3789 bp) consists of a roughly 1.1 kb HpaI-BsrGI *E. coli* genomic DNA fragment containing mcrA fused to the 2.7 kb BsgI-EcoRI fragment of pBR322.

pACYC-MHpaII was constructed by inserting the 2.0 kb HindIII fragment containing the hpaIIM gene (Card, C. O., et al. *Nucleic Acids Res*. 18:1377-1383 (1990)) into the HindIII site of pACYC184. The orientation of the insert is unknown, but M.HpaII expression was confirmed by complete protection of the construct from cleavage by HpaII.

DNA sequence. Nucleotide coordinates discussed in this work refer to the 1040 bp DNA sequence of the *E. coli* genomic fragment containing mcrA from GenBank accession no. Z19104 (Ramalingam, R., et al. *J. Biosci*. 17:217-232 (1992)). pJEK8 contains nt 35-1037 of this sequence, and the mcrA coding region is nt 124-957 of this sequence.

Bacteriophage restriction assays. All bacteriophage assays were performed on phage medium plates supplemented with 100 µg/mi ampicillin. Cross streak and spot tests were performed as described previously (Raleigh, E. A., et al. *Genetics* 122:279-296 (1989)). For full plate titers, 100 µl of cells prepared as for the spot tests were combined with 100 µl of bacteriophage (T4gt for RglA assays or λ methylated by M.HpaII for McrA assays) and incubated 20 minutes at room temperature. 2 ml of melted top agar were combined with the mixture and spread on phage plates supplemented with ampicillin.

Linker scanning mutagenesis. Mutagenesis was performed using the GPS-LS kit (New England Biolabs, Inc., Beverly, Mass.) according to the manufacturer's instructions.

The GPS-LS kit employs a Tn7-derived minitransposon carrying a selectable marker, with ends modified to encode PmeI sites at the penultimate positions (Biery, M. C., et al. *Nucleic Acids Res* 28:1067-77 (2000)). In an in vitro reaction including a transposon donor plasmid, a target DNA, and the transposase, the transposase excised the transposon from the donor and inserted it into the target. Five base pairs of target sequence were duplicated in the process, with one copy present at each side of the new insertion. The site of insertion was essentially random. The mutated target sequences were then transformed into a host cell such as ER1793, which is nonpermissive for donor plasmid replication. When a marker in the transposon was selected for, only transposition reaction products were recovered. In this case, the plasmid pJEK8, carrying mcrA, was used as a target, resulting in a collection of derivatives each with a single transposon insertion at a random location. Digestion of these derivatives with PmeI removed nearly the entire transposon, and recircularization left behind, at the original site of transposition, 15 bp not present in pJEK8: 10 bp were contributed by the residual transposon itself, and 5 bp by the target site duplication.

ER1793 cells were transformed by electroporation or chemical means with between 1 µl and 10 µl of the reaction mixture containing and selected with ampicillin and either kanamycin or chloramphenicol, depending on the donor plasmid used. Transformants were assayed by cross-streak, and plasmid was isolated from RglA$^-$ clones. 20 µl of each plasmid was digested with PmeI for 2 hours at 37° C. in a 50 µl volume, and the enzyme was heat killed by incubation for 20 min at 65° C. Half of each reaction was examined by gel electrophoresis to determine completeness of the reaction and correctness of fragment sizes. The remainder was ligated overnight at 16° C. with 400 units of T4 DNA ligase in a total volume of 100 µl. ER1793 cells were transformed again with 4 µl of each ligation reaction and selected with ampicillin. Transformants were assayed for RglA and/or McrA activity by cross-streak, spot test, or full plate titer. In addition, loss of the PmeI fragment containing the selectable marker was confirmed by restriction analysis. Insertions were located by DNA sequencing using the GPS-N and GPS-S primers (New England Biolabs, Inc., Beverly, Mass.).

Transposon insertion in pJEK 8 was achieved as described in Example 1. Transposon insertions in pJEK8 were generated and categorized using the rapid RglA phenotype classification. Only plasmids conferring the RglA⁻ phenotype were analyzed further. The precise location of the transposon insertion in each of these plasmids was determined by bidirectional sequencing from universal priming sites within the transposon. Next, the majority of the transposon was removed from each of the insertions by PmeI digestion and religation, generating a corresponding "linker insertion." These linker insertions contain a net of 15 bp (5 codons) of new sequence to pJEK8 at the site of the former transposon insertion. RglA and McrA phenotypes were then determined for each linker variant. Although all of the corresponding transposon insertions had been RglA⁻, the 15 bp insertions are substantially less disruptive than the full-length transposons. Indeed, RglA activity was restored for some but not all linker variants. Finally, for a selected set of linker variants, the ability to mediate DNA damage as revealed by SOS induction in the presence of M.HpaII was determined using a lacZ-based reporter system. Each step in the process will now be discussed in more detail.

Transposon mutagenesis. The mcrA-containing plasmid pJEK8 was mutagenized in vitro with minitransposons in 6 separate transposition reactions: five reactions employed the transposon "Transprimer-5" encoding resistance to kanamycin, and one used "Transprimer-4" encoding chloramphenicol resistance. Both transposons derive from Tn7, and were constructed such that the selectable marker can be deleted using PmeI. Following religation, a net of 15 new base pairs are left at the site of transposon insertion (Biery, M. C., et al. Nucleic Acids Res 28:1067-77 (2000)). When inserted into a coding sequence, these 15 bp are translated to five new amino acids in two of three reading frames; the third frame is not open, and results in a truncated protein product.

A total of 470 kanamycin- or chloramphenicol-resistant colonies were examined by cross-streak analysis, and 129 (27%) were scored as RglA⁻ (Table 1). It is here assumed that all insertions in the ampicillin-resistance marker and origin of replication are inviable, all transposon insertions in the mcrA coding region are RglA⁻, and all transposon insertions outside the mcrA coding region are RglA⁺. Given these assumptions, about 36% of transformants were expected to be RglA⁻ given a random distribution of insertions, in good agreement with the 27% obtained.

Transposon-insertion sites in those clones for which linker insertions were successfully obtained (a total of 84; see below) were located by DNA sequencing. In a large majority of cases, sequence data was obtained from two primers, GPS-N and GPS-S (New England Biolabs, Inc., Beverly, Mass.), reading out from the right and left ends of the transposon, respectively. In each of these cases the expected 5 bp target site duplication was present. In the few cases where sequence was obtained from only one of the two primers, the duplication was assumed to be present. In several cases where sequence data from GPS-N and GPS-S (New England Biolabs, Inc., Beverly, Mass.) was ambiguous or conflicting, sequence was obtained from the corresponding linker variant using independent primers hybridizing to the mcrA sequence. In all of these cases, the 15 bp insertion, including the 5 bp target site duplication, was present as expected.

Generation and analysis of linker variants. The target plasmid pJEK8 contained no PmeI sites, so digestion of the transposon insertion plasmids with PmeI generated two fragments: 3.8 kb (including all of pJEK8 plus 15 bp of new DNA at the site of transposon insertion; see FIG. 1) and either 1.7 kb or 1.4 kb (including the bulk of Transprimer-5 or Transprimer-4, respectively). Those of the PmeI-digested RglA⁻ clones which yielded the expected digest pattern were religated, yielding 3804 bp plasmids containing a functional origin of replication and encoding the McrA linker variants. Of the 129 RglA⁻ clones, 84 were used in the final analysis (Table 1).

Example II

Analysis of McrA Variants

Strategy for Analysis

The McrA variants made according to Example I were analyzed as follows:

(a) RglA activity: The linker variants were tested for RglA activity by spot test using phage T4gt. These showed a range of restriction greater than $10^6$-fold between the RglA⁺ phenotype (from ER1793[pJEK8] cells expressing wild-type McrA) and the RglA⁻ phenotype (from ER1793[pBR322] cells not expressing McrA). Tables 2 and 3 show the degree of restriction and corresponding phenotypes of 84 McrA variants with amino acid insertions or C-terminal truncations, respectively. Most variants resembled either the archetypal RglA⁺ or RglA⁻ phenotype, but several exhibited clearly intermediate degrees of T4gt restriction and were collectively termed RglA$^i$ phenotypes.

Linker variants were also tested for McrA activity by full plate titers with a stock of M.HpaII-methylated I phage that had been methylated and packaged in vitro (I.HpaII, $1.6 \times 10^6$ pfu/ml titered on ER1793[pBR322], with an approximate $5 \times 10^4$-fold range of restriction) (Kelleher, J., and E. A. Raleigh. *J. Bacteriol.* 173:5220-25223 (1991)). As with RglA assays, McrA⁺ and McrA⁻ phenotypes were determined on ER1793(pJEK8) and ER1793(pBR322) cells, respectively. Tables 2 and 3 show the degree of restriction and corresponding McrA phenotypes of linker variants with amino acid insertions or truncations, respectively. Those variants exhibiting clearly intermediate degrees of I.HpaII restriction were termed McrA$^i$ phenotypes.

(b) RglA classification of linker variants. Linker insertions generated by this method resulted in either in-frame amino acid insertions or premature stops depending on the reading frame. The amino acid insertions had varying composition, dependent partly on the target sequence at the site of insertion (FIG. 1). 56 such mutants were isolated, representing 46 independent locations within the gene and 42 independent locations within the protein. Of the 46 distinct mutants, 17 restricted T4gt to a degree approximating wild-type McrA (RglA⁺), 23 exhibited no detectable restriction (RglA⁻), and 6 restricted the phage but to a degree significantly less than the wild type (RglA⁺). FIG. 2 shows the distributions of these phenotypes across the gene graphically. Much of the protein is divided into tolerant and intolerant regions, judged by the clustering of green and red arrows. A segment within the modeled region contains a cluster of mutants with partial activity.

Figure 1:
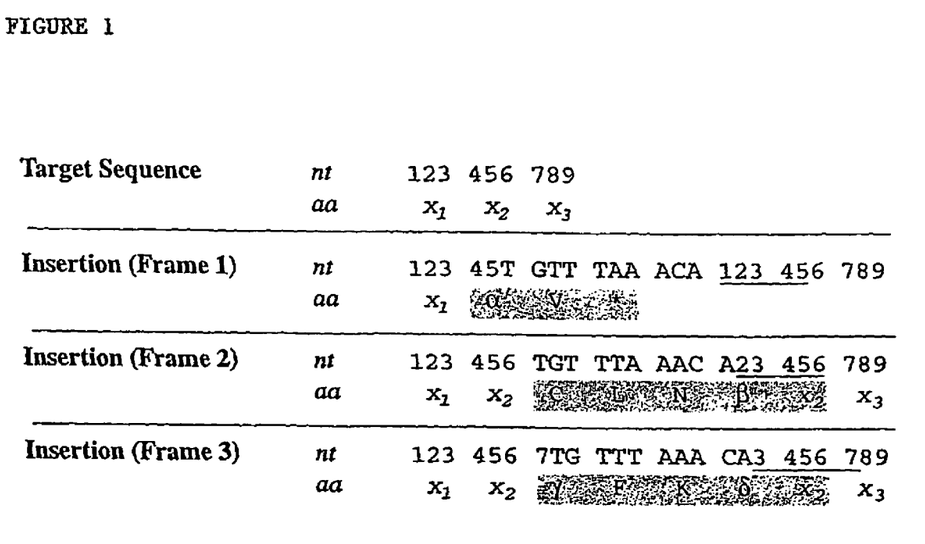

Truncation variants have linker insertions in frame 1 (FIG. 1). In this frame, the TAA sequence in the PmeI site is read as a stop codon, resulting in expressed proteins that are truncated at the point of insertion. 22 such variants were isolated, representing 20 distinct truncations. All of these variants were RglA⁻ with the exception of the C-terminal-most truncation, in which the last 9 residues of McrA (YVNINRLQK) are replaced with a single valine residue. This variant exhibited partial RglA activity (RglA$^i$). The amino acid insertions in this region were also RglA$^i$ (see Tables 2 and 3 and FIG. 2).

A group of variants, of which 6 were isolated, had linker insertions immediately upstream of the mcrA coding sequence. Although the expressed proteins should all be identical to wild type McrA, the original transposon insertions were no doubt RglA$^-$ due to separation of the coding sequence from its promoter. In agreement with this, all corresponding linker variants were RglA$^+$. Even clone 4-16, in which the distance between the putative ribosome binding site and the mcrA coding sequence was increased by 15 bp, appeared fully RglA$^+$.

(c) McrA classification of linker variants. In a surprisingly large number of cases (about ⅓ of all variants tested), the McrA phenotype did not match the RglA phenotype, confirming the separation of phenotype phenomenon observed in earlier studies (Hiom, K., and S. G. Sedgwick. *J. Bacteriol.* 173:7368-7373 (1991); Shivapriya, R., et al. Gene 157:201-7 (1995)). The relationship between the two phenotypes can be described by the following rules, with one exception.

(1) Variants that are RglA$^+$ are also McrA$^+$, and vice versa.
(2) Variants that are RglA$^i$ are also McrA$^i$.
(3) Variants that are RglA$^-$ can be either McrA$^-$ or McrA$^i$.

In most cases, RglA$^-$ variants with insertions or truncations in the N-terminal half are McrA$^-$, and RglA$^-$ variants with insertions or truncations in the C-terminal half were McrA$^i$.

To confirm that the McrA$^i$ phenotype observed in the truncation mutants did not result from spurious translational readthrough of the inserted stop codon, the AfeI-PmeI mcrA fragments from variants 2-24 (McrA$^i$) and 4-13 (McrA$^-$) were subcloned into the PmeI site of pNEB193. These subclones did not contain any mcrA-derived sequence downstream of the stop codon, but still conferred the same McrA phenotypes as their respective parental plasmids, indicating that the McrA$^i$ phenotype is intrinsic to the variant protein.

The single exception to the rules above is variant 1-75, which has a 5 amino acid insertion after residue 67 and is RglA$^-$ but fully McrA$^+$. All cases demonstrating separation of phenotype indicate that RglA activity is more easily disrupted by mutation than is McrA activity, or conversely, I.HpaII is more easily restricted than T4gt.

(d) Assessment of DNA damage. Whether McrA variants could mediate DNA damage was determined by induction of the LexA regulon (the "SOS response" to DNA damage) in the presence of M.HpaII methylation as previously shown for the wild type McrA (Piekarowicz, A., et al. *Nucleic Acids Res.* 19:1831-1835 (1991)). Each of the linker mutant plasmids was introduced into ER2171(pACYC-MHpaII), an *E. coli* reporter strain with lacZ fused to the damage-inducible dinD locus and expressing M.HpaII from a compatible plasmid. This strain yields blue colonies on X-gal plates at 37° C. and below when the SOS response has been induced. Similar reporter strains have been used to screen for restriction endonucleases and methyltransferases (Fomenkov, A., et al. *Nucleic Acids Res* 22:2399-403 (1994); Heitman, J., and P. Model. *J. Bacteriol.* 169:3243-3250 (1987); Piekarowicz, A., et al. *Nucleic Acids Res.* 19:1831-1835 (1991)).

The final columns of Tables 2 and 3 show the colony colors obtained in this test. As expected, pBR322 yielded white colonies, as did 12 of 15 derivatives with RglA$^-$McrA$^-$ phenotypes. No colonies were obtained from strains transformed with wild type or any derivatives with RglA$^+$McrA$^+$ phenotypes. This was anticipated also: strains containing mcrA restrict plasmids containing hpaIIM (Raleigh, E. A., and G. Wilson, *Proc. Nat'l. Acad. Sci. U.S.A.* 83:9070-9074 (1986)), so it is reasonable to expect that the opposite configuration of genes would also be incompatible. All RglA$^i$McrA$^i$ mutants yielded blue colonies, suggesting the presence of McrA-dependent DNA cleavage activity in these cases. 15 of 16 RglA$^-$McrA$^i$ mutants yielded white colonies, suggesting the absence of DNA cleavage activity. The partial restriction of I.HpaII by these mutants is therefore independent of apparent McrA nucleolytic activity and must result from some other mechanism.

There were a few exceptions to the above generalizations among the mutants with 5 amino acid insertions. One RglA$^-$McrA$^i$ mutant located in the middle of the protein yielded blue colonies. A more sensitive RglA assay indicated no more than 3-fold restriction of T4gt by this mutant. Although we consider restriction in this range to be RglA$^-$, the blue phenotype on X-gal suggests some level of DNA cleavage competence. Finally, three RglA$^-$McrA$^-$ insertion mutants in the middle of the protein yielded pale blue colonies on X-gal. This color did not appear until about 24 hours after plating and was significantly less intense than those scored as "blue." These variants were grouped with whites as discussed below.

(e) Distribution of insertions. The distribution of transposon insertions is shown in FIG. 2. Not shown are duplicate insertions. Nine of 72 sites yielded multiple insertions: one site had 4 insertions, one had 3 insertions, and 7 sites had 2 insertions. In 12 of the 16 possible pairs of duplicate insertions, the two members were generated by different transposition reactions and thus were independent.

The distribution of transposons appears random. The longest region that did not receive an insertion was between nucleotides 345 and 413 (68 bp long). Given a completely random distribution of 84 insertions in 872 bp (nt 85-957 in our sequence), the longest run of sequence observed without an insertion is approximately 67 bp which is compatible with the expected run length. (Expected run length was calculated as $K=\log_{1/(1-p)}N$, where K is the longest expected run, p=84/872 is the probability of an insertion at any given location, and N is the number of windows of size K, which is approximated as the sequence length 872.) Furthermore, no obvious biases were observed specific to either Transprimer-4 or Transprimer-5 (Tables 2 and 3).

TABLE 1

Summary of Linker Mutants Generated

| Experiment | Transposon | Cross-streak[a] | RglA- | Used[b] |
|---|---|---|---|---|
| 1 | Transprimer-5 | 100 | 21 | 13 |
| 2 | Transprimer-5 | 100 | 25 | 13 |
| 3 | Transprimer-5 | 99 | 35 | 24 |
| 4 | Transprimer-4 | 27 | 15 | 12 |
| 5 | Transprimer-5 | 45 | 12 | 10 |
| 6 | Transprimer-5 | 99 | 21 | 12 |
| Totals | | 470 | 129 | 84 |

[a]Number of transformants examined by cross-streak for loss of RglA activity.
[b]Number of RglA-clones used in the final analysis.

TABLE 2

Linker Variant Locations and Phenotypes (Amino Acid Insertions)

| Nucleotide | Amino acid | Residues inserted | Isolate number(s) | Phenotype RgIA[a] | McrA | SOS |
|---|---|---|---|---|---|---|
| n/a | n/a | n/a | pBR322 | − | − | white |
| n/a | n/a | n/a | pJEK8 | + | + | x |
| 85 | n/a | n/a | 3-58 | + | | |
| 108 | n/a | n/a | 1-2 | + | | |
| 112 | n/a | n/a | 1-39 | + | | |
| 115 | n/a | n/a | 3-27 | + | | |
| 117 | n/a | n/a | 5-32 | + | | |
| 124 | 0 | MFKHI | 1-66 | + | | |
| 125[b] | n/a | n/a | 4-16 | + | | |
| 133 | 3 | LFKHV | 6-19 | + | + | |
| 168 | 15 | CLNKC | 1-20, 1-68, 3-42, 6-97 | + | + | |
| 184 | 20 | VFKQE | 4-11, 4-21 | + | + | |
| 208 | 28 | VFKHL | 4-22 | − | − | white |
| 235 | 37 | MFKQN | 3-29 | − | − | white |
| 237 | 38 | CLNNK | 5-45 | − | − | white |
| 238 | 38 | VFKHK | 3-89 | − | − | white |
| 256 | 44 | VFKHL | 5-30 | − | − | white |
| 261 | 46 | CLNNY | 2-85, 3-34, 5-49 | − | − | white |
| 271 | 49 | LFKHE | 3-21 | − | − | pale blue |
| 298 | 58 | VFKHQ | 5-34 | + | + | x |
| 303 | 60 | CLNIV | 5-57 | + | + | x |
| 313 | 63 | VFKHL | 3-55 | − | − | pale blue |
| 324 | 67 | CLNTS | 1-75 | − | + | mixed[c] |
| 345 | 74 | CLNNS | 3-17 | + | + | x |
| 418 | 98 | MFKHL | 1-24, 2-47 | − | − | white |
| 423 | 100 | CLNKM | 3-33 | − | − | pale blue |
| 432 | 103 | CLNSY | 3-36 | − | − | white |
| 477 | 118 | CLNTG | 4-3 | + | + | x |
| 490 | 122 | LFKQK | 3-8, 3-22 | − | i | blue |
| 495 | 124 | CLNRI | 3-66 | − | − | white |
| 508 | 128 | LFKHV | 1-54 | + | + | x |
| 594 | 157 | CLNTL | 1-77 | + | + | |
| 597 | 158 | CLNIL | 6-16 | + | + | |
| 600 | 159 | CLNMN | 2-66 | + | + | |
| 625 | 167 | MFKHK | 6-98 | + | + | x |
| 640 | 172 | LFKHQ | 3-57 | − | i | white |
| 645 | 174 | CLNTE | 4-12 | + | + | |
| 646 | 174 | VFKHE | 3-30 | + | + | |
| 654 | 177 | CLNTR | 4-6 | + | + | |
| 655 | 177 | MFKHR | 6-6 | + | + | x[d] |
| 696 | 191 | CLNIR | 3-24 | − | i | white |
| 715 | 197 | LFKQA | 6-58 | − | i | white |
| 732 | 203 | CLNKS | 1-33 | i | i | blue |
| 774 | 217 | CLNIY | 6-28 | i | i | blue |
| 795 | 224 | CLNTY | 3-18 | i | i | pale blue |
| 798 | 225 | CLNNL | 1-42 | − | i | white |
| 810 | 229 | CLNNH | 2-6 | − | i | white |
| 828 | 235 | CLNTS | 1-84 | − | i | white |
| 829 | 235 | VFKHS | 5-66 | − | i | white |
| 874 | 250 | LFKQN | 6-18 | − | i | white |
| 876 | 251 | CLNNC | 6-12 | − | i | white |
| 921 | 266 | CLNIE | 2-5, 4-27 | i | i | blue |
| 925 | 267 | LFKQM | 1-57, 3-48 | i | i | blue |
| 937 | 271 | MFKHN | 3-46 | i | i | blue |

[a] Both RgIA and McrA phenotypes are defined as follows: − (<10 fold restriction), i ("intermediate", 10-1000 fold restriction), + (>1000 fold restriction).
[b] Insertion here is in frame 1, but results only in additional nucleotides upstream of the start codon, not in truncation of the expressed protein.
[c] Variant 1-75 yielded a mixture of both white and blue colonies on X-gal.
[d] Variant 6-6 yielded several white colonies when transformed at high concentration.

TABLE 3

Linker Variant Locations and Phenotypes (Protein Truncations).

| Nucleotide | Amino acid | Residues inserted | Isolate number(s) | RgIA | McrA | SOS |
|---|---|---|---|---|---|---|
| 134 | 4 | V* | 3-45 | − | | |
| 143 | 7 | V* | 3-56 | − | | |
| 170 | 16 | V* | 4-23 | − | | |
| 194 | 24 | V* | 2-80 | − | | |
| 224 | 34 | V* | 5-55, 5-61 | − | | |
| 269 | 48 | DV* | 4-10, 6-56 | − | − | white |
| 413 | 97 | V* | 5-38 | − | − | |
| 419 | 98 | NV* | 2-56 | − | − | |
| 476 | 118 | V* | 6-77 | − | − | |
| 497 | 124 | FV* | 2-49 | − | − | |
| 509 | 129 | V* | 4-13 | − | − | |
| 569 | 149 | V* | 2-24 | − | i | white |
| 761 | 213 | V* | 2-55 | − | i | white |
| 770 | 216 | V* | 3-26 | − | i | white |
| 773 | 217 | V* | 4-17 | − | i | white |
| 788 | 222 | V* | 2-42 | − | i | white |
| 830 | 236 | V* | 6-83 | − | − | white |
| 869 | 249 | V* | 2-46 | − | − | white |
| 881 | 252 | SV* | 2-81 | − | i | white |
| 926 | 268 | V* | 3-7 | i | i | blue |

What is claimed is:

1. An isolated *E. coli* McrA variant able to cleave DNA comprising methylcytosine but not hydroxymethylcytosine, the variant comprising an amino acid sequence which differs from the amino acid sequence of its parent *E. coli* McrA polypeptide solely by:
   (a) a modification at a position corresponding to amino acid 67 of SEQ ID NO: 2; or
   (b) a modification at a position corresponding to amino acid 67 of SEQ ID NO: 2 and at one or more positions selected from the group consisting of those corresponding to amino acids 3, 15, 20, 58, 60, 74, 118, 128, 157, 158, 159, 167, 174, and 177 of SEQ ID NO: 2.

2. The *E. coli* McrA variant according to claim 1, wherein the *E. coli* McrA variant is encoded by a gene which results from making one or more mutations in the polynucleotide of SEQ ID NO: 1.

3. A method for separating methylated DNA from unmethylated DNA, comprising:
   (a) immobilizing one or more *E. coli* McrA variants according to claim 1;
   (b) contacting the one or more *E. coli* McrA variants with a DNA sample;
   (c) selectively binding DNA containing methylated cytosine residues; and
   (d) separating methylated DNA from unmethylated DNA.

4. A method for identifying methylated DNA comprising:
   (a) binding one or more *E. coli* McrA variants according to claim 1 to a DNA substrate; and
   (b) identifying the extent and optionally the location of binding of the *E. coli* McrA variants by means of a reporter tag, thus identifying the DNA substrate as methylated.

5. The method according to claim 4, wherein the reporter tag is a fluorescent, chemiluminescent or radioactive tag.

6. A method for selectively cleaving methylated DNA, comprising mixing DNA with a preparation comprising the *E. coli* McrA variant of claim 1 under conditions suitable for cleavage of the DNA at methylation sites in the DNA.

7. The method according to claim 6, wherein the nucleotide sequences of the methylation sites are selected from the group consisting of $C^{5m}CGG$, $C^{5m}CSGG$, and $^{5m}CG$.

* * * * *